(12) United States Patent
Godfrey et al.

(10) Patent No.: US 10,620,103 B2
(45) Date of Patent: Apr. 14, 2020

(54) DEVICES AND METHODS FOR EVALUATING THE SPREADABILITY OF POWDERS UTILIZED IN ADDITIVE MANUFACTURING

(71) Applicant: HONEYWELL INTERNATIONAL INC., Morris Plains, NJ (US)

(72) Inventors: Donald G. Godfrey, Phoenix, AZ (US);
Brian G. Baughman, Surprise, AZ (US); Mark McNair, Gilbert, AZ (US);
Henry A. Lastre, Phoenix, AZ (US);
Derrick Guthrie, Mesa, AZ (US);
Justin Schnepf, Mesa, AZ (US);
Robert Kielbus, Tempe, AZ (US);
John Dolan, Tempe, AZ (US);
Ethanial Harms, Mesa, AZ (US);
Matthew Figueroa, Mesa, AZ (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

(21) Appl. No.: 15/979,986

(22) Filed: May 15, 2018

(65) Prior Publication Data
US 2019/0353569 A1 Nov. 21, 2019

(51) Int. Cl.
*B33Y 40/00* (2020.01)
*G01N 11/10* (2006.01)
(Continued)

(52) U.S. Cl.
CPC .............. *G01N 11/10* (2013.01); *B33Y 40/00* (2014.12); *B33Y 50/00* (2014.12); *B33Y 70/00* (2014.12);
(Continued)

(58) Field of Classification Search
CPC .............................................. G01N 11/10–167
See application file for complete search history.

(56) References Cited

U.S. PATENT DOCUMENTS

2003/0117622 A1* 6/2003 Sevick-Muraca ............................ G01N 15/0211 356/338
2013/0183189 A1* 7/2013 Bishop ................... B22F 9/082 419/62
(Continued)

FOREIGN PATENT DOCUMENTS

| CN | 106846335 A | 6/2017 |
|---|---|---|
| CN | 106984816 A | 7/2017 |

(Continued)

OTHER PUBLICATIONS

Slotwinski et al., "Characterization of Metal Powders Used for Additive Manufacturing", Sep. 16, 2014, Journal of Research of the NIST, p. 460-493 (Year: 2014).*

(Continued)

*Primary Examiner* — Robert J Hance
(74) *Attorney, Agent, or Firm* — Lorenz & Kopf, LLP

(57) ABSTRACT

Devices (herein "powder spreadability inspection tools") and methods are provided for evaluating the spreadability of powders utilized in additive manufacturing (AM) processes. In embodiments, the powder spreadability inspection tool includes a powder support surface on which a visual inspection area is provided, a spreader system including a spreader implement, and a powder dispenser. The spreader implement is movable relative to the powder support surface along a path, which extends or passes over the visual inspection area. The powder dispenser is operable to dispense a pre-measured or metered volume of an AM powder sample onto the powder support surface ahead of the spreader implement. As the spreader implement moves along the path relative to the powder support surface, the spreader implement spreads a layer of the metered powder sample across the visual (Continued)

inspection area to allow a visual evaluation of the spreadability of the AM powder.

18 Claims, 9 Drawing Sheets

(51) Int. Cl.
*B33Y 50/00* (2015.01)
*B33Y 70/00* (2020.01)
*G01N 15/00* (2006.01)
*B22F 3/105* (2006.01)

(52) U.S. Cl.
CPC ............ *G01N 15/00* (2013.01); *B22F 3/1055* (2013.01); *G01N 2015/0096* (2013.01)

(56) References Cited

U.S. PATENT DOCUMENTS

| | | | | |
|---|---|---|---|---|
| 2013/0343947 | A1* | 12/2013 | Satzger | B22F 3/1055 419/55 |
| 2015/0165683 | A1* | 6/2015 | Cheverton | G06T 7/0004 382/141 |
| 2015/0177158 | A1* | 6/2015 | Cheverton | G01N 15/0227 700/119 |
| 2016/0002471 | A1* | 1/2016 | Peng | C09C 3/06 428/403 |
| 2017/0038342 | A1* | 2/2017 | Clavette | B33Y 40/00 |
| 2017/0066192 | A1* | 3/2017 | Cho | G01B 11/2513 |
| 2017/0090462 | A1* | 3/2017 | Dave | G01N 21/00 |
| 2017/0120337 | A1* | 5/2017 | Kanko | B22F 3/1055 |
| 2018/0004192 | A1 | 1/2018 | Perret et al. | |
| 2018/0009165 | A1* | 1/2018 | Agawa | B29C 64/153 |
| 2018/0126487 | A1* | 5/2018 | Chen | B33Y 30/00 |
| 2018/0322621 | A1* | 11/2018 | Craeghs | G01N 21/8851 |
| 2019/0039318 | A1* | 2/2019 | Madigan | B29C 64/393 |
| 2019/0041312 | A1* | 2/2019 | Hadar | G01N 15/1425 |
| 2019/0047228 | A1* | 2/2019 | Brown | B29C 64/153 |
| 2019/0070787 | A1* | 3/2019 | Higgs, III | G06N 3/04 |
| 2019/0105843 | A1* | 4/2019 | Saharan | B29C 64/393 |
| 2019/0134754 | A1* | 5/2019 | Jacquemetton | B22F 3/1055 |
| 2019/0257766 | A1* | 8/2019 | Yang | B22F 3/1055 |

FOREIGN PATENT DOCUMENTS

| | | |
|---|---|---|
| WO | 2014095200 A1 | 6/2014 |
| WO | 2018024210 A1 | 2/2018 |

OTHER PUBLICATIONS

Guthrie, M.; HP Accelerates Digital Reinvention of Manufacturing Industry with Open Platform . . . , Retrieved from Internet May 15, 2018 [https://press.ext.hp.com/us/en/press-releases/2017/hp-accelerates-digital-reinvention-of-ma . . . ].

Zelinski, P., HP Supports Material Development with Open Lab and Kit for Testing Spreadability; Retrieved from internet May 15, 2018 [https://www.additivemanufacturing.media/blog/post/hp-supports-material-development-wi . . . ].

Goehrke, S.A.; Introducing the MDK: SigmaDesign & HP Present Material Development Kit for HP Multi Jet Fusion Open 3D Printing Platform; Retrieved from Internet May 15, 2018 [https://3dprint.com/168338/hp-sigmadesign-mdk/].

* cited by examiner

DEVICES AND METHODS FOR EVALUATING THE SPREADABILITY OF POWDERS UTILIZED IN ADDITIVE MANUFACTURING

TECHNICAL FIELD

The following disclosure relates generally to additive manufacturing and, more particularly, to devices (herein "powder spreadability inspection tools") and methods for evaluating the spreadability of powders utilized in additive manufacturing processes.

Abbreviations

Abbreviations appearing relatively infrequently in this document are defined upon initial usage, while abbreviations appearing more frequently in this document are defined below.
AM—Additive manufacturing;
DMLS—Direct metal laser sintering;
FOV—Field-of-view;
ROM—Range of motion;
SEM—Scanning electron microscope; and
SLS—Selective laser sintering.

BACKGROUND

ATSM International has established several standards for evaluating certain characteristics of metallic and non-metallic powders utilized in selective fusion- or sinter-based AM processes. Generally, the established standards for AM powders pertain to various measures of powder flow rates and densities. However, there exist few, if any established standards or standardized tools for evaluating AM powder spreadability; that is, the ease and consistency with which a given AM powder can be physically distributed in a continuous layer of substantially uniform thickness utilizing a spreading motion, such as a motion similar to that of a recoater contained in a powder bed AM machine.

The lack of convenient tools and standardization for assessing the spreadability of AM powders can be problematic in that powder morphology (particle size and shape) can vary significantly between powder suppliers, production lots, and material types. Moreover, the atomization processes commonly employed to produce AM powders may yield powders having substantial variance in morphology within the same production lot. The usage of AM powders having sub-optimal spreadabilities can detract from the reliability and performance of AM machines; and, in certain cases, may degrade the structural integrity of components fabricated from the such powders. Consequently, in instances in which a selected AM powder is loaded into an AM machine, and it is only subsequently discovered that the selected powder possesses a poor spreadability, removal of the powder from the machine may be warranted. Depending upon machine design, AM powder removal can be a cumbersome and time-consuming process, which prolongs machine downtime, suppresses throughput, and increases the overall cost and duration of the AM process.

An ongoing demand thus exists for the provision of devices and methods useful in assessing the spreadability of powders utilized in AM processes. Ideally, such devices and methods would enable rapid visual evaluation of powder spreadability in a reliable and consistent manner to, for example, support the establishment of commonly-accepted standards governing powder spreadability. It would also be desirable if, in at least some embodiments, such devices and methods were capable of emulating the spreading action of a recoater of the type commonly found in powder bed AM machines. Other desirable features and characteristics of embodiments of the present invention will become apparent from the subsequent Detailed Description and the appended Claims, taken in conjunction with the accompanying drawings and the foregoing Background.

BRIEF SUMMARY

Devices (herein "powder spreadability inspection tools") are provided for evaluating the spreadability of powders utilized in AM processes. In various embodiments, the powder spreadability inspection tool includes a powder support surface on which a visual inspection area is provided, a spreader system including a spreader implement, and a powder dispenser. The spreader implement is movable relative to the powder support surface along a path, which extends or passes over the visual inspection area. The powder dispenser is operable to dispense a premeasured or metered volume of an AM powder sample onto the powder support surface ahead of the spreader implement. As the spreader implement moves along the path relative to the powder support surface, the spreader implement spreads a layer of the metered powder sample across the visual inspection area to allow a visual evaluation of the spreadability of the AM powder. The visual evaluation can be performed manually or, instead, may be automated utilizing computer imaging system.

In other embodiments, the powder spreadability inspection tool includes a powder support surface having a visual inspection area, a spreader system configured to spread the AM powder over the visual inspection area as a powder layer having a substantially uniform thickness, and visual indicia on the powder support surface correlating coverage of the visual inspection area of the powder layer with a spreadability quality of the AM powder. The visual indicia can be, for example, color-coded regions of the visual inspection area. In certain implementations, the spreader system may include: (i) a wiper blade spaced from the powder support surface by a vertical gap, as taken along an axis orthogonal to the powder support surface; and (ii) a spreader actuator configured to move the wiper blade from a start position to an end position to spread the powder layer over the visual inspection area.

Methods for evaluating AM powder spreadability are also provided. Generally, the methods are carried-out utilizing a powder spreadability inspection tool, which includes a spreader implement and a powder support surface having a visual inspection area thereon. In certain implementations, the method includes the steps or processes of: (i) dispensing a predetermined amount of an AM powder sample onto the powder support surface; (ii) utilizing the spreader implement to spread the AM powder sample across the visual inspection area, with the AM powder sample distributed or spread in a powder layer having a substantially uniform thickness; and (iii) visually assessing the spreadability of the AM powder sample based, at least in part, on a degree to which the powder layer covers the visual inspection area. In certain implementations, the spreader implement may include a lower edge spaced from the powder support surface by a vertical gap having a height, as taken along a first axis orthogonal to the powder support surface. In such implementations, the step or process of dispensing may include dispensing the AM powder sample in a predetermined amount sufficient to cover at least a majority of the visual inspection area, given the height of the vertical gap, when the AM powder sample possesses an optimal spreadability.

Various additional examples, aspects, and other useful features of embodiments of the present disclosure will also become apparent to one of ordinary skill in the relevant industry given the additional description provided below.

BRIEF DESCRIPTION OF THE DRAWINGS

At least one example of the present invention will hereinafter be described in conjunction with the following figures, wherein like numerals denote like elements, and.

For simplicity and clarity of illustration, descriptions and details of well-known features and techniques may be omitted to avoid unnecessarily obscuring the exemplary and non-limiting embodiments of the invention described in the subsequent Detailed Description. It should further be understood that features or elements appearing in the accompanying figures are not necessarily drawn to scale unless otherwise stated.

DETAILED DESCRIPTION

The following Detailed Description is merely exemplary in nature and is not intended to limit the invention or the application and uses of the invention. The term "exemplary," as appearing throughout this document, is synonymous with the term "example" and is utilized repeatedly below to emphasize that the description appearing in the following section merely provides multiple non-limiting examples of the invention and should not be construed to restrict the scope of the invention, as set-out in the Claims, in any respect.

Definitions

The following definitions apply throughout this document. Those terms not expressly defined here or elsewhere in this document are assigned their ordinary meaning in the relevant technical field.

Additive Manufacturing (AM) powder—any powderized or particulate material utilized in selective fusion- or sinter-based AM processes (defined below), regardless of composition.

Direct Metal Laser Sintering (DMLS)—A selective laser sintering (SLS) process in which a metallic AM powder is utilized.

Fusion-based or sinter-based Additive Manufacturing (AM) process—any additive manufacturing process in which an energy source, such as a laser or electron beam, is impinged upon selected regions of powder layers to build-up parts, components, or articles of manufacture on a layer-by-layer basis in accordance with computer-readable three dimensional object data.

Recoater—any device or mechanism that dispenses or applies fresh layers of AM powder over a powder bed utilized in an AM process, such as SLS or DMLS.

Selective Laser Sintering (SLS)—any additive manufacturing process in which a laser beam is impinged upon selected regions of powder layers to build-up parts on a layer-by-layer basis in accordance with computer-readable three dimensional object data. This term encompasses the more specific term "DMLS."

OVERVIEW

Figure 1:
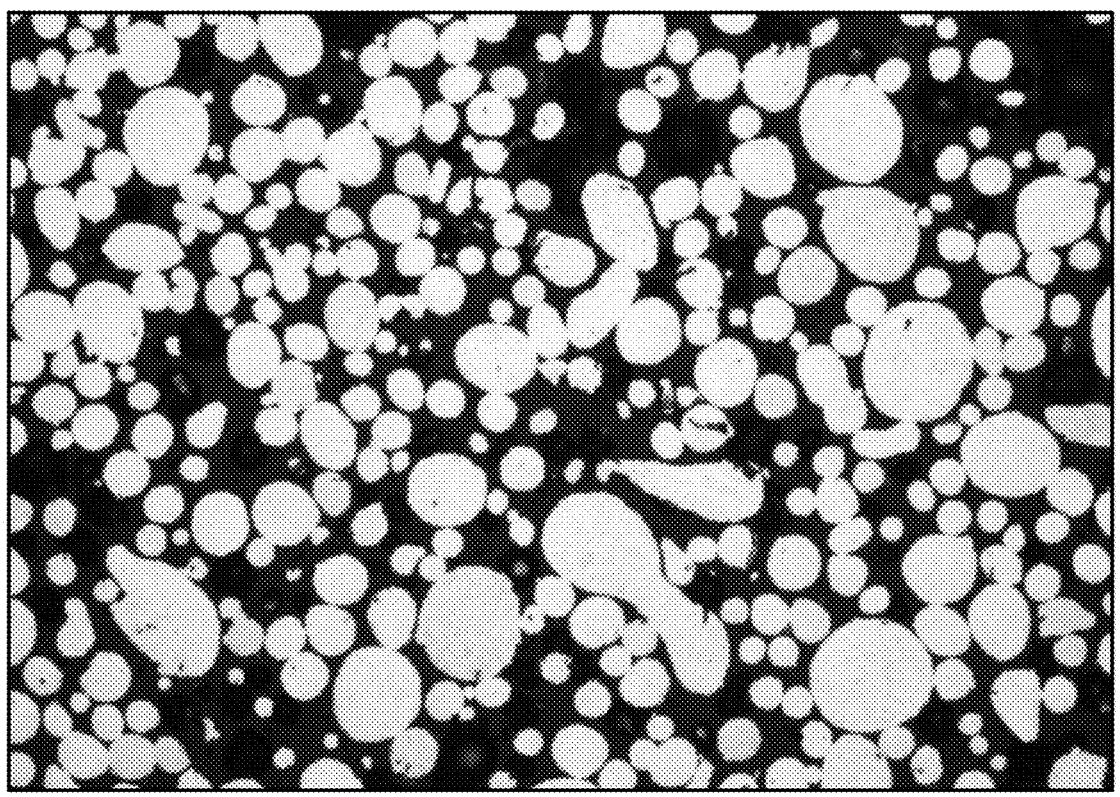
FIG. 1 is an SEM image of a generalized AM powder, which demonstrates the variance in powder morphology (size and shape) potentially occurring within a single powder lot.

As discussed above, relatively few, if any methods or devices presently exist for evaluating the spreadability of AM powders in a repeatable and consistent manner, as appropriate to support the establishment of industry standards governing powder spreadability. This deficiency is problematic, particularly considering that significant variances in powder morphology (particle size and shape) can occur between manufacturers, production lots, and materials. Additionally, non-trivial variances in powder morphology have been observed within a single production lot, whether produced via powder atomization or utilizing other fabrication techniques, as indicated in the SEM image of the generalized AM powder shown in FIG. 1. Due to such potential disparities in powder morphology, the various issues set-forth above (e.g., decreased build quality and throughput, prolonged machine downtime and manufacturing schedules, and higher manufacturing costs) can result when an AM powder having a poor or sub-optimal spreadability is inadvertently utilized in the fabrication of AM components.

To mitigate or overcome the above-described issues, the following provides devices powder spreadability inspection tools and methods for assessing the spreadability of powders utilized in AM processes. Generally, embodiments of the powder spreadability inspection tools operate by spreading AM powder samples over a support surface having a visual inspection area. A given AM powder sample may be spread in a layer having a substantially uniform thickness utilizing a spreader implement, which may emulate a recoater mechanism of type utilized in powder bed AM machines. After a layer of an AM powder sample has been spread across the visual inspection area, spreadability of the powder sample can be evaluated by visually examining the physical distribution of the newly-spread powder layer and, specifically, the degree to which the powder layer covers various regions of the visual inspection area. Visual inspection of the newly-spread powder layer can be performed manually or, instead, may be automated; that is, carried-out utilizing a computer imaging system, which analyzes imagery of the newly-spread powder layer captured by at least one camera having an FOV encompassing the visual inspection area. If desired, graphics (e.g., a scale) or other visual indicia for reference in assessing powder spreadability can be provided on or adjacent the visual inspection area. For example, in one embodiment, different regions of the visual inspection area may be coded to varying colors to provide an intuitive indication of spreadability quality.

The powder spreadability inspection tools set-forth below enable screening of AM powders to ensure that such AM powders satisfy minimum spreadability criteria prior to usage in AM component fabrication. Such screening or powder inspection can be performed upon initial receipt of raw material or after reworking, sifting, mixing, or otherwise modifying the AM powders in some respect. Regardless, the usage of such powder spreadability inspection tools and methods allows AM powders possessing poor or sub-optimal spreadability characteristics to be identified and addressed prior to usage and, preferably, prior to loading into an AM machine. By aiding in the identification of AM powders having sub-optimal spreadabilities prior to usage, embodiments of the inspection tools and methods can bring about favorable reductions in AM machine downtime, improve manufacturing efficiency, and lower overall manufacturing costs. Additionally, the usage of such inspection tools and methods can potentially improve the average powder quality or uniformity utilized in the production of AM components and, perhaps, may support the establishment of industry standards for powder spreadability. An exemplary embodiment of a powder spreadability inspection tool will now be described in conjunction with FIGS. 2-9. The following description is provided by way of non-limiting example only, with the understanding that alternative embodiments of the inspection tool are also contemplated and equally viable.

Exemplary Embodiment of a Powder Spreadability Inspection Tool

Figure 2:
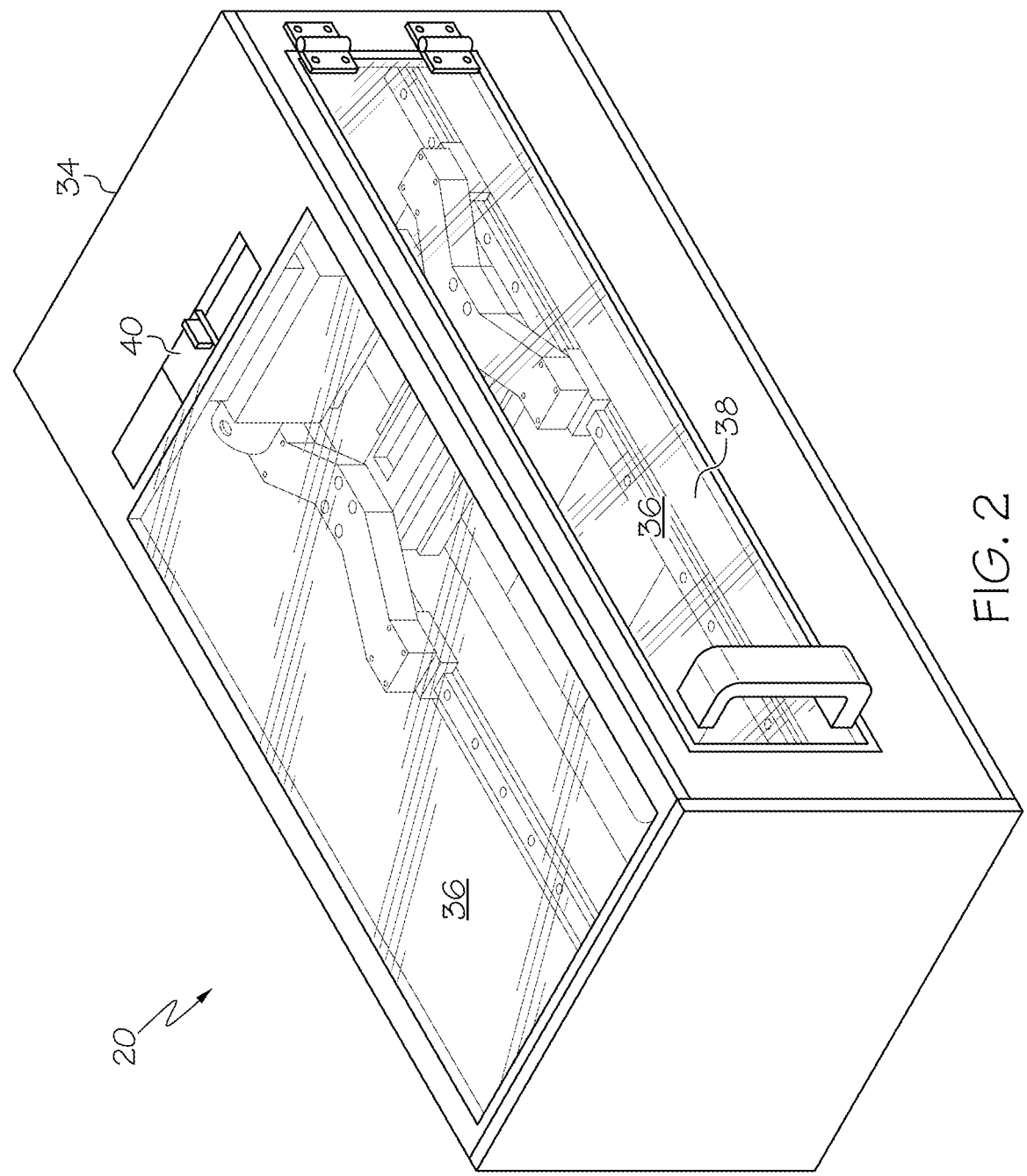
FIGS. 2 and 3 are isometric views of an exemplary powder spreadability inspection tool for evaluating the spreadability of AM powder samples, as illustrated with and without an enclosure, respectively.
Figure 3:
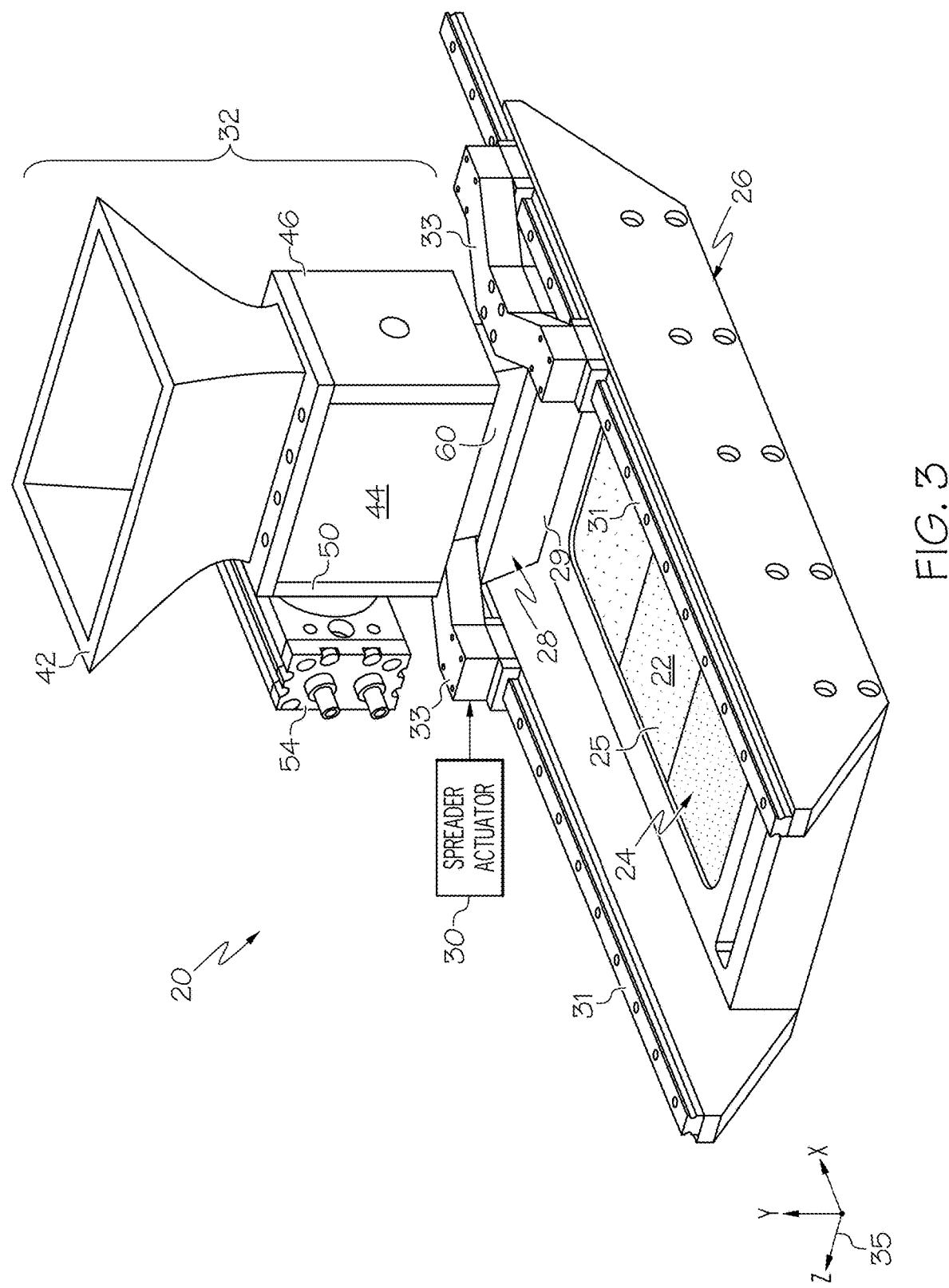

FIGS. 2 and 3 are isometric views of an exemplary powder spreadability inspection tool 20, as illustrated in accordance with an exemplary embodiment of the present disclosure. Powder spreadability inspection tool 20 includes a visual inspection area 22 (identified in FIG. 3) across which AM powder samples are spread, cleared, and re-spread, as appropriate, to allow visual assessments of powder spreadability. Visual inspection area 22 is located on a horizontally-oriented surface 24, hereafter "powder support surface 24." In the illustrated example, powder support surface 24 is defined by the upper principal surface of a base plate 25 (identified in FIG. 3), which is contained in a larger base, frame, or chassis 26 of inspection tool 20. In other embodiments, powder support surface 24 may be defined by a different structural element or combination of elements, providing that surface 24 and visual inspection area 22 are characterized by generally planar topologies and surface finishes suitable for serving as substrates over which AM powder samples are spread. As indicated in FIGS. 2-3, visual inspection area 22 may occupy the substantial entirety of powder support surface 24; however, this is not necessary in all embodiments. Base plate 25 and, more generally, chassis 26 may have an electrically-conductive (e.g., aluminum) construction to allow electrical grounding in at least some embodiments, particularly when inspection tool 20 is utilized to test atomized metallic powders susceptible to ignition. Thus, in such embodiments, base plate 25 may be referred to as an "electrically-grounded plate," which defines powder support surface 24.

In certain implementations of powder spreadability inspection tool 20, visual inspection area 22 is sized to have a width substantially equivalent to the width of the lower edge of the below-described spreader implement; the "width" of area 22 and the spreader implement measured along an axis parallel to support surface 24 and corresponding to the Z-axis identified by coordinate legend 35 in FIG. 3. Further, the surface area encompassed by visual inspection area 22 may be dimensioned such that, when dispensed in a sample size of an appropriate volume, an AM powder sample possessing an optimal spreadability can be distributed across visual inspection area 22 in a substantially continuous layer of uniform thickness, while covering the majority, if not the substantial entirety of visual inspection area 22. Thus, in such implementations, a specific mathematical relationship may exist between the surface area encompassed by visual inspection area 22, the metered volume of the AM powder samples dispensed by powder dispenser 32 (described below), and the layer thickness at which the sample powder is spread. This relationship is discussed more fully below in conjunction with FIGS. 7-9. First, however, additional description of exemplary powder spreadability inspection tool 20 is provided in connection with FIGS. 2-6.

With continued reference to FIGS. 2-3, and as shown most clearly in FIG. 3, powder spreadability inspection tool 20 further contains a spreader device or system 28. In the illustrated example, spreader system 28 includes a spreader implement 29, a spreader actuator 30, and a linear guide system 31, 33. Spreader implement 29 is movable with respect to chassis 26 and powder support surface 24 along a translational axis, which extends parallel to surface 24 and corresponds to the X-axis identified by coordinate legend 35. Linear guide system 31, 33 confines movement of spreader implement 29 to movement along the translational axis and, specifically, to motion along a substantially straight or linear path extending over visual inspection area 22. Linear guide system 31, 33 includes parallel guide rails 31, which extend upwardly from opposing sidewalls of chassis 26; and a number of sliding mount brackets 33, which engage guide rails 31 for sliding movement along rails 31. Sliding mount brackets 33 may contain ball or other rolling element bearings in an embodiment. Sliding mount brackets 33 are further fixedly joined to spreader implement 29 and, thus, cooperate with parallel guide rails 31 to confine movement of implement 29 to linear movement along the translational axis, as described.

Spreader actuator 30 is operable to move spreader implement 29 along the translational axis from a START position (shown in FIGS. 2-3) to an END position. As schematically shown in FIG. 3, spreader actuator 30 can assume any form suitable for performing this function, including that of an electric, hydraulic, or pneumatic actuator, or a combination thereof. In certain embodiments, spreader actuator 30 assumes the form of a non-electrical actuator, such as a pneumatic actuator, which may help decrease the likelihood of electrical sparking that could otherwise potentially ignite an atomized powder cloud in certain instances. In such embodiments, spreader actuator 30 may further include an air directional control valve to prevent over-travel of spreader implement 29.

In the exemplary embodiment shown in FIGS. 2-3, spreader implement 29 moves relative to an external or "real-world" frame of reference during each iteration of powder spreading, while chassis 26 and powder support surface 24 remain spatially fixed with respect to such an external frame of reference. In alternative realizations of inspection tool 20, powder support surface 24 may move relative to an external frame of reference as an AM powder sample is spread across visual inspection area 22, while spreader implement 29 may concurrently move with respect to the external frame of reference or may instead remain static or spatially fixed with respect thereto. To provide a more specific example, in an alternative embodiment, powder support surface 24 may be defined by a movable substrate, such as rotatable plate or a conveyor belt, which moves beneath spreader implement 29 to induce relative motion between surface 24 and implement 29 and thereby spread AM powder samples across area 22, when appropriate. Various other modifications are also possible, providing that spreader implement 29 is movable relative to powder support surface 24 in a manner allowing AM powder samples to be spread in layers across visual inspection area 22 for assessment of powder spreadability.

Powder spreadability inspection tool 20 further contains a powder dispenser 32. Powder dispenser 32 can assume any form and include any number of components for selectively dispensing a premeasured or "metered" volume of AM powder samples ahead or forward of spreader implement 29, as taken along the path traveled by implement 29 when moving from the START position (shown in FIGS. 2-3) to the END position (shown in FIGS. 8-9, described below). In the embodiment shown in FIGS. 2-3, powder dispenser 32 is positioned to reside above spreader implement 29 when in the START position and may be fixedly coupled to chassis 26 through enclosure 34 (described below). Consequently, powder dispenser 32 does not move in conjunction with spreader implement 29 when traveling along the translational axis from the START position to the END position in the illustrated example. In other implementations, however, powder dispenser 32 may be affixed to spreader implement 29 and move in conjunction therewith.

In certain cases, and as shown exclusively in FIG. 2, powder spreadability inspection tool 20 may further include an outer casing, housing, or enclosure 34. When provided, enclosure 34 may protect the moving components of powder spreadability inspection tool 20, while containing (e.g., acrylic) viewing windows 36 to allow visual inspection (manual or automated) of the visual inspection area following each iteration of the below-described test process. Additionally, enclosure 34 may include various other features supportive of the operation and maintenance of powder spreadability inspection tool 20, such a manual access door 38 and a powder inlet port 40. Powder inlet port 40 may be provided in an upper portion of enclosure 34 to provide physical access to an inlet of powder dispenser 32; e.g., inlet port 40 may feed into the mouth of a hopper further included in powder dispenser 32, as described below in conjunction with FIG. 4.

As are many of the components contained in exemplary powder spreadability inspection tool 20, viewing windows 36 of enclosure 34 are non-essential and need not be included in all embodiments. For example, in alternative embodiments, viewing windows 36 may be rendered unnecessary via the integration of one or more cameras into the interior of enclosure 34. In such embodiments, still images or live feeds from the camera or cameras within inspection tool 20 can be presented on a display screen and manually inspected (e.g., viewed by a technician) in evaluating the spreadability of AM powder samples. Otherwise, such imagery captured by cameras can be supplied to a processing architecture for image analysis when an automated inspection approach is employed. In this latter case, such image processing can be performed onsite by an image analysis system located in the same physical vicinity as the tested AM powders; or, instead, image analysis can be outsourced or "offboarded" to a remotely-located entity, such as a cloud-based service or server farm, which communicates with the image analysis system over the Internet or other network. Further discussion in this regard is set-forth below in conjunction with FIG. 7.

Figure 4:
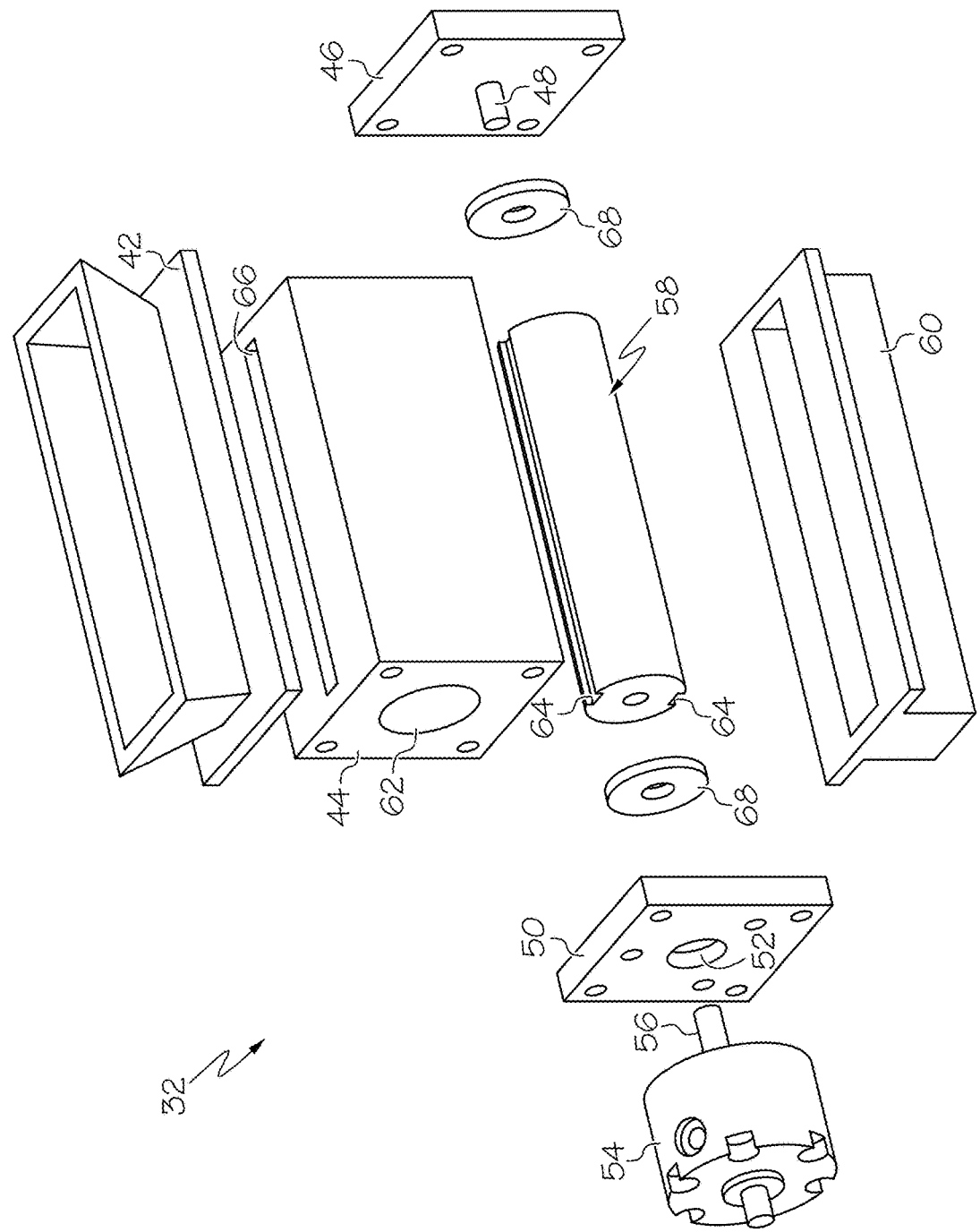
FIG. 4 is an exploded view of a powder dispenser suitably contained in the exemplary powder spreadability inspection tool shown in FIGS. 2 and 3.

Turning next to FIG. 4, powder dispenser 32 is illustrated in an exploded view. Progressing generally from top to bottom in FIG. 4, powder dispenser 32 includes an upper hopper 42, a central housing or main case 44, an idle end cap 46 from which a central post 48 extends, a piston end cap 50 through which a central opening 52 is provided, a rotary actuator 54 having an output shaft 56, a rotating metering shaft or pin 58, and a lower powder funnel 60. A generally cylindrical central channel or bore 62 is provided through main case 44. When powder dispenser 32 is fully assembled as shown in FIG. 3, metering pin 58 is received within bore 62 and can rotate relative to main case 44 and the other static component of dispenser 32. Also, when powder dispenser 32 is assembled, idle end cap 46 is positioned adjacent a first end or side of main case 44 such that post 48 extends into an opening provided in metering pin 58. Similarly, piston end cap 50 is positioned adjacent the opposing side of main case 44, with shaft 56 of rotary actuator 54 extending through opening 52 of end cap 50 and into an aligning opening provided in the opposing end of metering pin 58. Shaft 56 is rotationally fixed relative to metering pin 58. Thus, as rotary actuator 54 is actuated, output shaft 56 of actuator 54 and metering pin 58 co-rotate or turn in unison over a desired angular ROM.

Two slots or metering troughs 64 are formed in an outer circumferential portion of metering pin 58 and spaced by an angular offset of 180 degree (°), as taken about the periphery of pin 58. In other implementations, a different number of metering troughs 64 may be provided in metering pin 58 and spaced about the periphery thereof. During operation of inspection tool 20, an AM powder sample is drawn from hopper 42 and flows downwardly under the influence of gravity into an upper slot 66 provided in case 44. Continuing to flow downwardly, the AM powder sample then fills the metering trough 64 currently positioned immediately beneath the outlet of hopper 42 and slot 66. When appropriate, rotary actuator 54 is then actuated to rotate metering pin 58 by a 180° angular ROM about its rotational axis, thereby rotating the newly-filled trough 64 into a downwardly-facing orientation and dispensing (or, more informally, "dumping") the metered powder sample into powder funnel 60. In the illustrated example, rotary actuator 54 assumes the form of a pneumatic piston, which, as noted above, may help decrease the likelihood of spark generation should powder cloud ignition be of concern. This notwithstanding, rotary actuator 54 can assume various other forms (e.g., electric, hydraulic, or manually-operated) in further embodiments of inspection tool 20.

In addition to discharging the AM powder sample from the previously-filled trough 64, rotation of metering pin 58 in the above-described manner further positions the empty metering trough 64 beneath hopper 42 and slot 66. In this manner, the empty metering trough 64 is immediately presented for filling with any powder remaining in hopper 42, thereby facilitating subsequent test iterations. In further embodiments, the volume or capacity of metering troughs 64 may be adjustable by, for example, the reception of inserts. Alternatively, metering troughs 64 of varying dimensions (e.g., a range of depths) can be formed in metering pin 58 to allow the dispensed volume of AM test powder to be adjusted by controlling the angular position or clocking of metering pin 58 within main case 44 during the powder dispensing process. In this latter case, a valve may be positioned in the powder flow path near the bottom of case 44 to prevent the inadvertent filling of the non-selected metering troughs. Various other types of powder metering systems can also be incorporated into powder spreadability inspection tool 20 in place of powder dispenser 32 in further implementations.

Upon receiving the AM powder sample from metering pin 58, powder funnel 60 guides or directs the powder sample into spreader system 28. Spreader implement 29 further directs the powder sample onto powder support surface 24 at a location forward or ahead of spreader implement 29, as taken along the path along which implement 29 travels, for subsequent distribution across visual inspection area 22. The dispensed powder sample may or may not be routed through implement 29 prior to contacting powder support surface 24, as discussed below in connection with FIGS. 5-6. If desired, and as further shown in FIG. 4, felt seals 68 may be disposed on opposing sides of metering pin 58 to help retain the metered powder samples within troughs 64 with minimal spillage. Although not shown in FIGS. 2-6, various other gaskets or other seals can be included in powder dispenser 32 and, more broadly, in inspection tool 20, as appropriate.

Figure 5:
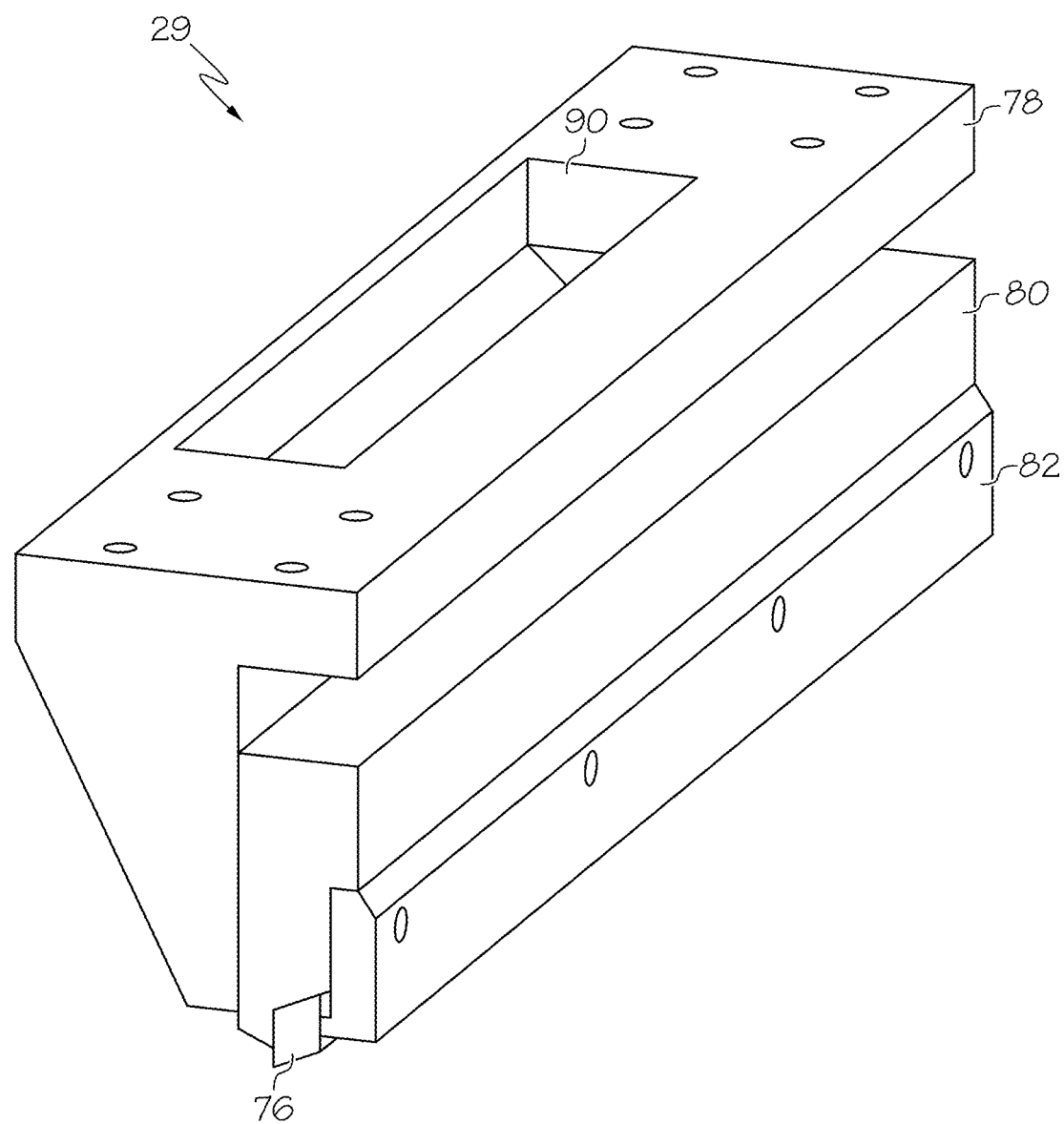
FIGS. 5 and 6 are isometric and cross-sectional views, respectively, of a spreader system further contained in the exemplary powder spreadability inspection tool shown in FIGS. 2 and 3.
Figure 6:
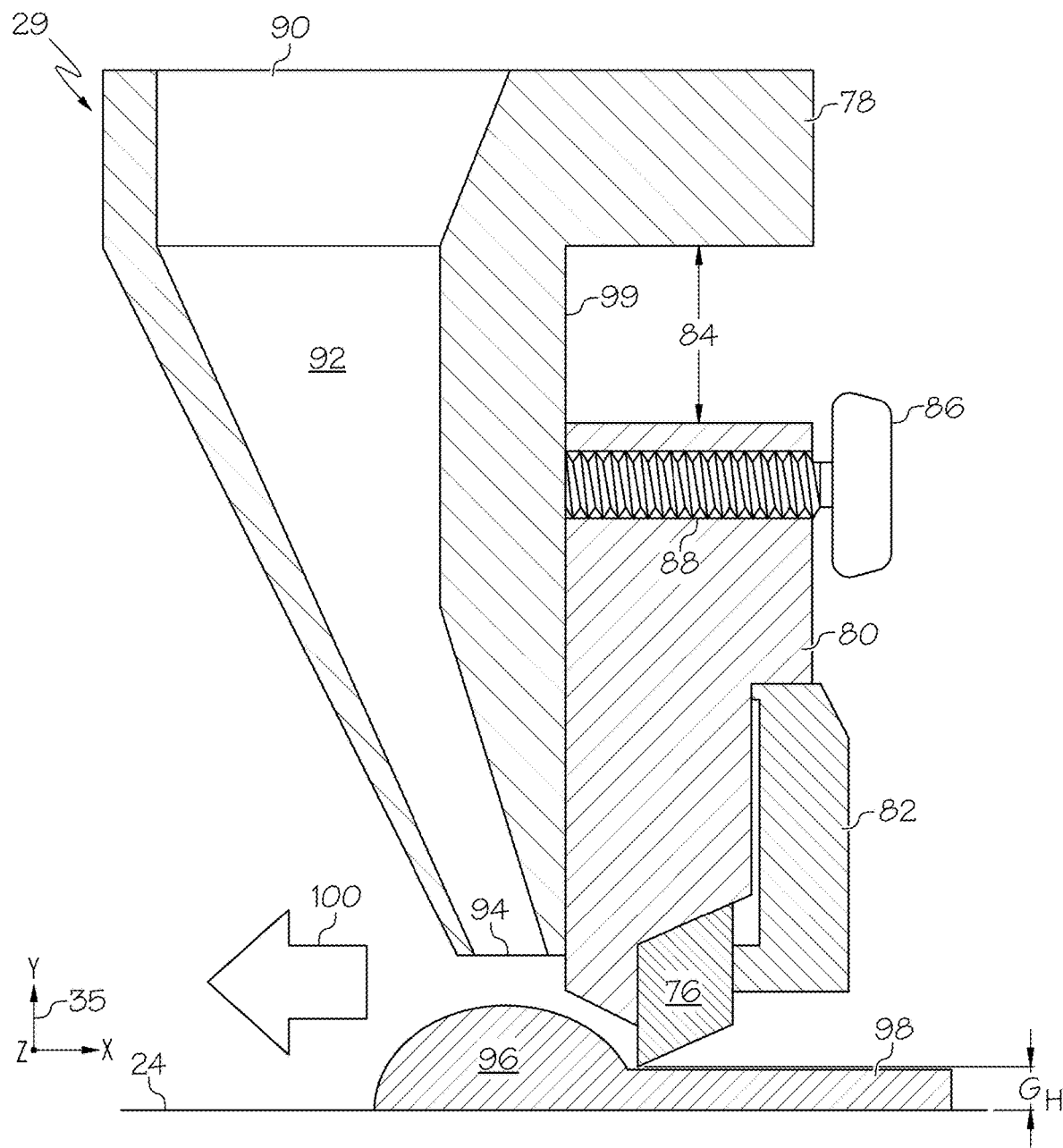

Spreader implement 29 will now be described in greater detail with reference to FIGS. 5 and 6. Here, spreader implement 29 is a blade-type implement, which carries a wiper blade 76 defining the lower edge of implement 29 and contacting the AM powder samples during movement of implement 29 and spreading of the powder samples. In other realizations, spreader implement 29 may include a different structural element, such as a roller, which defines the lower edge of implement 29 and which is suitable for distributing AM powder samples in a layer of substantially uniform thickness across visual inspection area 22 (FIG. 3). In addition to wiper blade 76, spreader implement 29 contains a fixed-height blade mount or blade carriage 78, a height-adjustable blade mount 80, and a retainer bar or blade clamp 82. As shown, blade clamp 82 secures wiper blade 76 against height-adjustable blade mount 80. Blade mount 80 attaches wiper blade clamp 82 to blade carriage 78, while allowing the vertical height or elevation of wiper blade 76 to be adjusted to preference. Lastly, blade carriage 78 joins blade mount 80 to sliding mount brackets 33 of linear guide system 31, 33; and, in certain embodiments, may help direct dispensed powder samples to a desired location ahead of wiper blade 76.

Height-adjustable blade mount 80 can be positioned and re-positioned, as desired, to varying vertical heights with respect to blade carriage 78; the term "height," as appearing herein, referring to a dimension measured along an axis orthogonal to powder support surface 24 (corresponding to the Y-axis of coordinate legend 35). This adjustability is indicated in FIG. 6 by double-headed arrow 84, which identifies the clearance or spacing between an upper portion of height-adjustable blade mount 80 and a trailing ledge of blade carriage 78. Further, and as shown exclusively in FIG. 6, a thumb or set screw 86 may be provided to secure blade mount 80 in a desired vertical position relative to blade carriage 78. Specifically, the threaded shaft of set screw 86 is received in a threaded channel 88 provided through blade mount 80. The terminal end of set screw 86 abuts blade carriage 78 to frictionally retain blade mount 80 in a desired position when screw 86 is tightened. When the vertical height of blade carriage 78 is adjusted, so too is the vertical height of wiper blade 76 and the height of the gap separating the lower edge of wiper blade 76 from powder support surface 24. The height of this gap is identified as gap "$G_H$" in FIG. 6. The height of the gap $G_H$ between the lower edge of blade 76 and surface 24 may be substantially uniform or constant, taken across the length of blade 76 (that is, along an axis orthogonal to the translational axis and parallel to power support surface 24; corresponding to the Z-axis of coordinate legend 35), such that implement 29 spreads AM powder samples in layers of substantially uniform thickness.

As indicated above, the illustrated embodiment of spreader implement 29 includes a height adjustment mechanism allowing the height of blade mount 80 (and, therefore, the gap height $G_H$) to be selected from an infinite or continuous (rather discrete) range of settings within the vertical ROM of blade mount 80. If desired, a scale (e.g., hatch marks labeled in millimeters) or other graphics may be provided on spreader implement 29 (e.g., on back surface 99 of height-fixed blade carriage 78) to denote the set gap height $G_H$, as determined by the vertical position in which blade mount 80 is secured. In alternative embodiments, height-adjustable blade mount 80 may be movable through a number of discrete positions and secured in a desired position utilizing a different locking mechanism, such as a spring-loaded plunger. It still other realizations, an automated mechanism (e.g., a linear actuator or a rotary actuator and a leadscrew) may be utilized to adjust the vertical position of blade mount 80. As a still further possibility, the vertical position of blade mount 80 (and, therefore, wiper blade 76) with respect to powder support surface 24 may be fixed.

When provided, the adjustability of gap height $G_H$ allows a technician or other personnel member to set the layer thickness at which AM powder samples are spread across powder inspection area 22. For example, a technician may set the layer spread thickness to be substantially equivalent to the thickness at which the AM powder will be spread by a recoater (or similar device) including a powder bed AM machine, which is subsequently utilized to produce AM components from the sampled powder. Additionally or alternatively, gap height $G_H$ may be selected with respect to the surface area of visual inspection area 22 such that, when dispensed in an appropriately-metered volume, an AM powder sample having an optimal spreadability can be spread across visual inspection area 22 in manner providing complete or substantially complete coverage of area 22.

In certain embodiments, powder dispenser 32 may dispense metered volumes of AM powder samples ahead of spreader implement 29 without directing the powder through implement 29. In other embodiments, the dispensed powder may be directed through spreader implement 29 by gravity flow after discharge from powder dispenser 32. For example, and with continued reference to FIGS. 5-6, a powder guide channel 90 may be provided through spreader implement 29. Guide channel 90 includes an inlet 92 formed in an upper region of blade carriage 78 for receiving dispensed powder from metering pin 58 included in powder dispenser 32. Guide channel 90 further includes an outlet 94, which is positioned to direct a body of powder 96 onto support surface 24 immediately ahead of wiper blade 76. Specifically, outlet 94 may be dimensioned and oriented to discharge powder body 96 in a substantially linear or elongated pile, which has a width (as taken the Z-axis of coordinate legend 35) substantially equivalent to that of wiper blade 76. As implement 29 moves along its predetermined path in the direction indicated by arrow 100, wiper blade 76 distributes dispensed powder body 96 over powder support surface 24 and visual inspection area 22 as a spread powder layer 98 having a substantially uniform thickness equivalent to gap height $G_H$.

Figure 7:
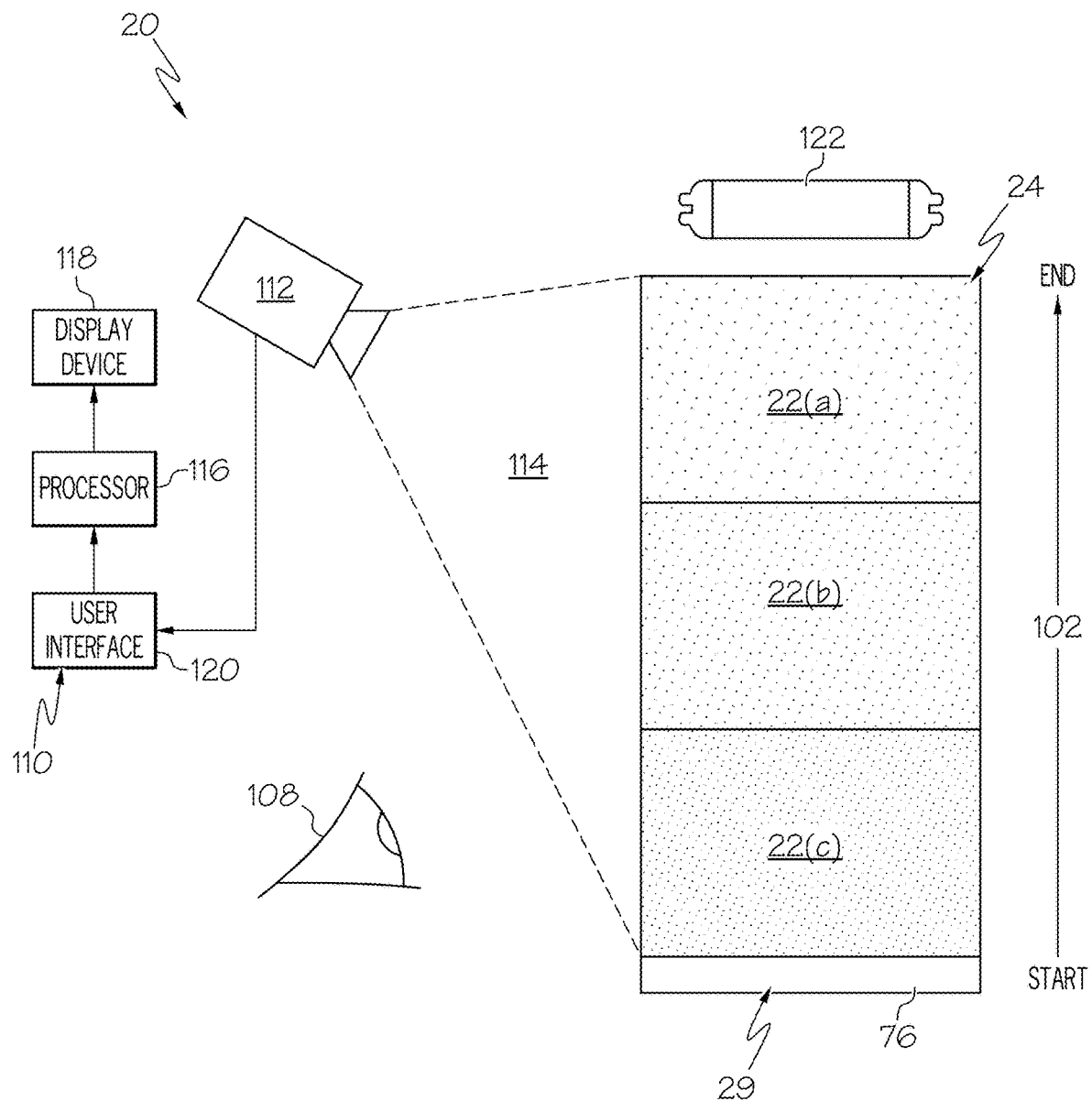
FIG. 7 illustrates the visual inspection area of the inspection tool shown in FIGS. 2-3, as seen from a top-down or planform viewpoint, and further illustrates a block diagram of a computer imaging system for automating visual inspection of powder spreadability.

Progressing to FIG. 7, powder support surface 24 and visual inspection area 22 are shown from a top-down or planform perspective. In this example, visual inspection area 22 is divided into three visually distinct regions 22(a)-(c). The region adjacent the START position of spreader implement 29 is identified as proximal region "22(c)," the region furthest from the START position of implement 29 is identified as distal region "22(a)," and the region between regions 22(a), (c) is identified as intermediate region "22(b)." When moving along the linear path represented by arrow 102 from the START position to the END position (labeled on the right side of FIG. 7), spreader implement 29 spreads powder across visual inspection area 22. If possessing a poor spreadability, the newly-spread layer of the AM powder sample will generally provide incomplete coverage of visual inspection area 22. For example, AM powder possessing a highly poor spreadability may only provide appreciable coverage of proximal region 22(c), with lesser (if any) coverage of intermediate region 22(b), and still lesser (if any) coverage of region 22(c).

Figure 8:
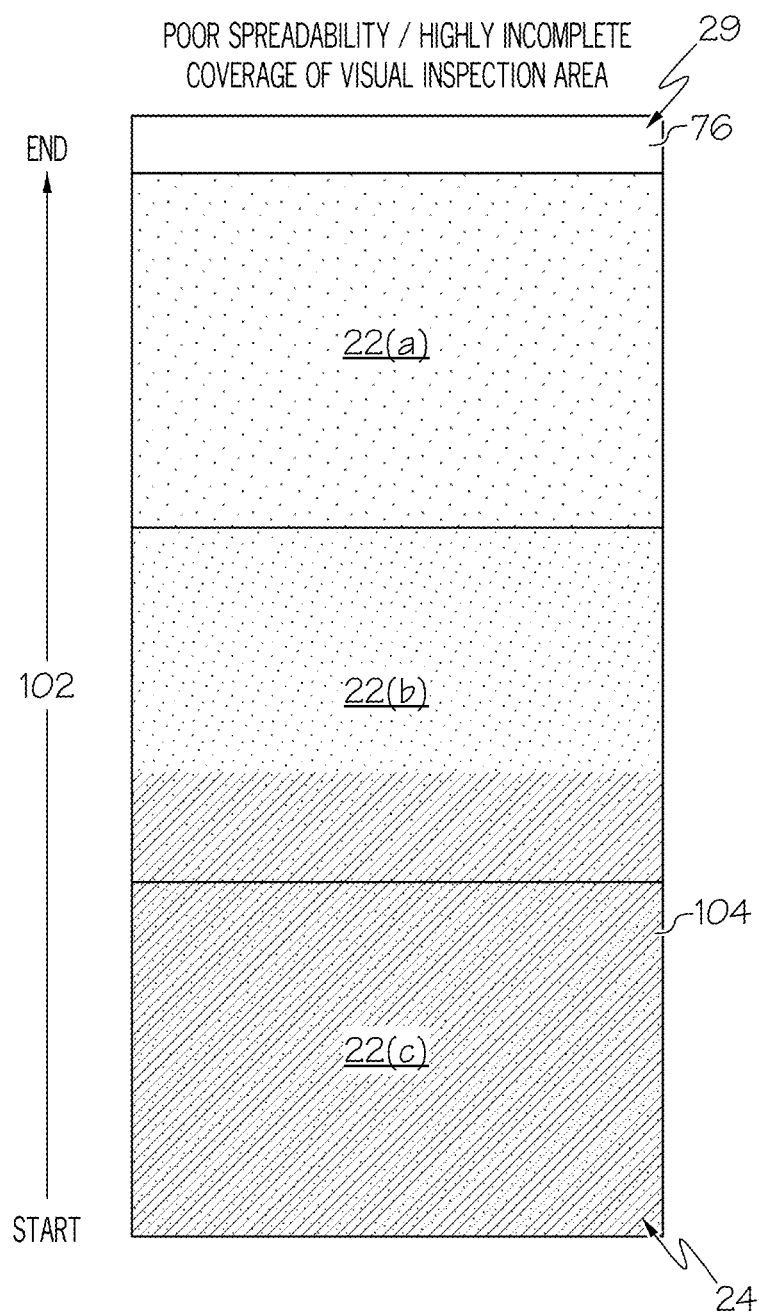
FIGS. 8 and 9 are planform views of the visual inspection area of the exemplary powder spreadability inspection tool shown in FIGS. 2, 3, and 7, as illustrated following spreading of two AM powder samples having sub-optimal and optimal spreadabilities, respectively.

An example of a newly-spread layer 104 of an AM powder sample having such poor spreadability is shown in FIG. 8. Comparatively, an AM powder sample possessing a spreadability of moderate quality may provide a more thorough, but still incomplete coverage of visual inspection area 22; e.g., such a powder may provide fairly complete coverage of proximal region 22(c), moderate coverage of intermediate region 22(b), and incomplete coverage of distal region 22(a). Finally, an AM powder having a good or optimal spreadability may provide substantially complete coverage of visual inspection area 22, considered in its entirety. An example of a newly-spread layer 106 of an AM powder sample having such optimal spreadability is further depicted in FIG. 9. As can be seen in this drawing figure, the newly-spread powder layer 106 provides substantially complete coverage of regions 22(a)-(c) of visual inspection area 22.

Markings or other visual indicia for reference when evaluating the spreadability of a newly-spread powder layer are usefully provided on or adjacent visual inspection area 22. For example, a hatched scale or textual read-outs, which correlate powder coverage to spreadability quality, can be provided adjacent inspection area 22 for reference in implementations of inspection tool 20. In alternative embodiments, the visual indicia can assume various other forms. In many cases, the visual indicia (when provided) will include a first visual indicator of a poor powder spreadability adjacent the start position of spreader implement 29, a second visual indicator of good powder spreadability adjacent the end position of implement 29, and any number of visual indicators of intermediate power spreadability quality between the first and second visual indicators.

Figure 9:
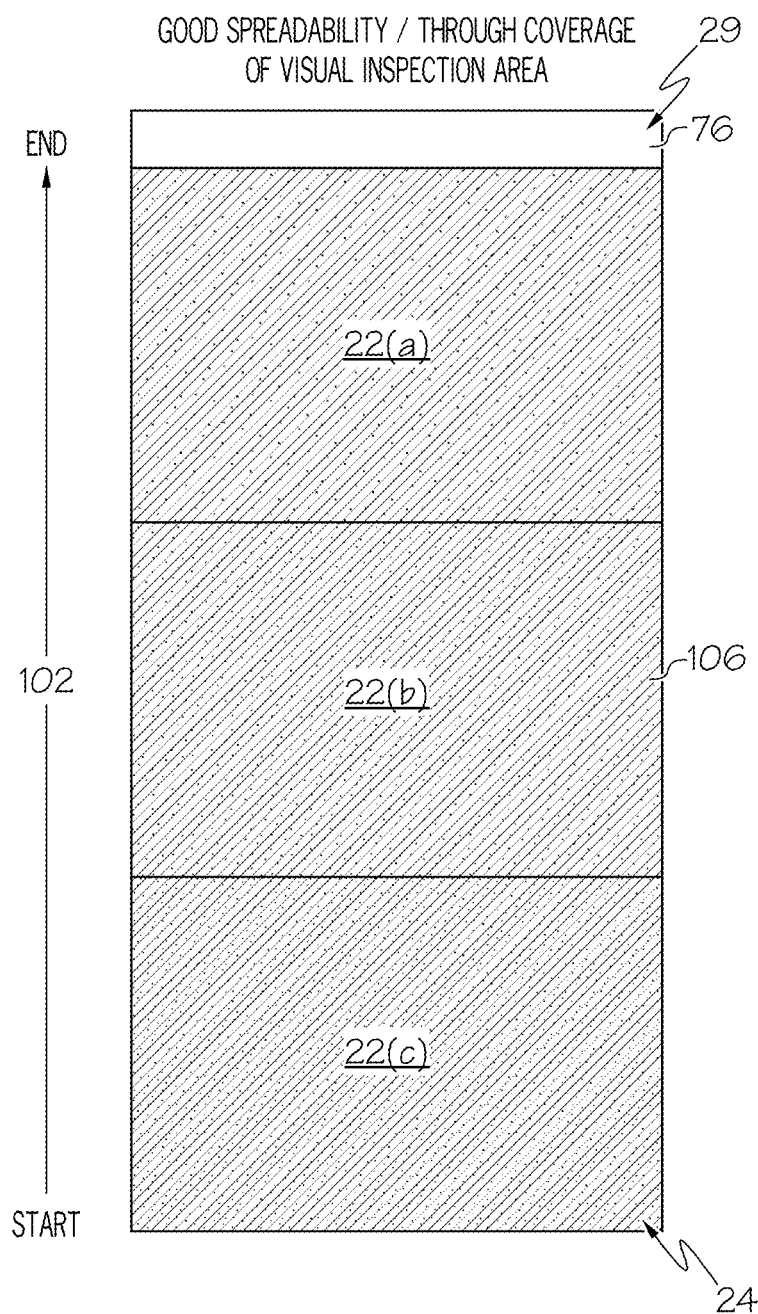

In certain embodiments, and as indicated in FIGS. 7-9 by differing cross-hatch patterns, regions 22(a)-(c) may each be coded a different color; e.g., by anodization of base plate 25 defining powder support surface 24, when plate 25 is composed of aluminum or another material capable of anodization. In such embodiments, proximal region 22(c) may be color-coded to warning color (e.g., red), intermediate region 22(b) to a caution color (e.g., amber or yellow), and distal region 22(a) to an informational or advisory color (e.g., green). In this manner, a technician examining a newly-spread layer of an AM test powder is provided with an intuitive visual cue or reference system for gaging powder spreadability. Specifically, in this case, the technician may conclude that the powder sample has demonstrated poor spreadability if an appreciable amount of red-coded proximal region 22(a) is visible after spreading of the powder layer. If red-coded proximal region 22(a) is largely covered by powder, while an appreciable amount of yellow-coded intermediate region 22(b) is visible after spreading of a powder layer, the powder sample has demonstrated a fair spreadability. Finally, if only a portion of green coded distal region 22(a) is visible (with fairly complete coverage of regions 22(b),(c)), or if all regions 22(a)-(c) are covered by the newly-spread powder sample, the technician may conclude powder sample has demonstrated an optimal spreadability.

As noted above, inspection of newly-spread powder layers can be performed manually by a human observer and/or automated utilizing a computerized image analysis system. The possibility of manual inspection of visual inspection area 22 post powder-spreading is represented in FIG. 7 by human eye icon 108, while the possibility of automatic or computerized inspection is indicated by a block diagram of computerized image analysis system 110. As schematically illustrated, image analysis system 110 may includes at least one camera 112 having a FOV 114, which encompasses visual inspection area 22. A processor 116 is operably coupled to camera 112 and receives imaging data therefrom. The singular term "processor," as appearing herein, is utilized for convenience of reference and encompasses any number and type of processors, and similar microelectronic components or logic structures, which may be operably interconnected to support the processing capabilities of system 110. Processor 116 or, more generally, system 110 also contains a memory or storage area containing computer-readable instructions or code executed by processor 116 when performing the steps or functionalities described herein.

Following and, perhaps, during spreading a layer of an AM powder sample across visual inspection area 22, camera 112 captures imagery (still or a live video feed) of the newly-spread powder layer and provides this imagery data to processor 116 for analysis. Processor 116 may then analyze the imagery by, for example, comparison to stored templates or images of powder samples correlated to varying powder spreadability quality levels. When powder spreadability is determined, corresponding visual cues may be generated on a display device 118 operably coupled to processor 116. For example, a text annunciation may be presented on display device 118 indicating whether the newly-tested powder possesses a low, moderate, or high quality of spreadability. In other embodiments, processor 116 may generate an alert on display device 118 only when the spreadability of a newly-tested AM powder sample is determined to be of poor or sub-optimal quality. In other embodiments, image analysis system 110 may transmit image data obtained from camera 112 to a remotely-located entity, such as a cloud-based service or server farm, for processing. The remotely-located entity may then provide responsive data indicating the assessed spreadability level or quality of tested powder sample, which processor 116 may then indicate on display device 118.

A user interface 120 may further be included in image analysis system 110 to allow entry of user input to, for example, specify the values of variable parameters for a given test iteration conducted utilizing tool 20. This may include, for example, the entry of data specifying the set gap height and powder type. In certain embodiments, other aspects of powder spreadability inspection tool 20 may also be controlled utilizing user interface 120, such as the movement of spreader implement 29, operations of powder dispenser 32, and the like. Finally, as indicated in the upper right of FIG. 7, at least one light source 122 may be provided to illuminate visual inspection area 22. When a powder spreadability is evaluated by a human observer, light source 122 may be standard light source emitting light within the visible spectrum. However, when a computerized visual inspection approach is employed, light source 122 can potentially emit light outside of the visible spectrum, as detectable utilizing camera 112 and suitable for enhancing image processing of newly-spread powder layers. It is also possible for visual inspection area 22 to be underlit or illuminated from a light source beneath (or potentially embedded within base plate 25) in implementations in which powder support surface 24 is at least partially translucent.

CONCLUSION

The foregoing has provided powder spreadability inspection tools for evaluating the spreadability of AM powders utilized in a fusion- or sinter-based AM processes, such as SLS and DMLS processes. During usage of such tools, an AM powder sample is dispensed onto the support surface ahead of the spreader implement in a predetermined or metered volume, which may be tailored with respect to the surface area of the visual inspection area and a gap height between the spreader implement and the support surface, to allow complete or substantially complete coverage of the visual inspection area by the powder layer when possessing a good or optimal spreadability. After spreading of the AM powder sample, the distribution and coverage of the newly-spread powder layer may be visually assessed to evaluate the spreadability quality of tested AM powder. In this manner, the spreadability of AM powders can be assessed prior to usage in AM processes, whether upon receipt of raw material; after reworking, mixing, or sifting an AM powder; or at any other desired juncture. This, in turn, may result in a decrease in AM machine downtime, an improvement in manufacturing costs and expediency, and an enhancement to the average powder quality utilized to produce AM components.

Terms such as "comprise," "include," "have," and variations thereof are utilized herein to denote non-exclusive inclusions. Such terms may thus be utilized in describing processes, articles, apparatuses, and the like that include one or more named steps or elements, but may further include additional unnamed steps or elements. While at least one exemplary embodiment has been presented in the foregoing Detailed Description, it should be appreciated that a vast number of variations exist. It should also be appreciated that the exemplary embodiment or exemplary embodiments are only examples, and are not intended to limit the scope, applicability, or configuration of the invention in any way. Rather, the foregoing Detailed Description will provide those skilled in the art with a convenient road map for implementing an exemplary embodiment of the invention. Various changes may be made in the function and arrangement of elements described in an exemplary embodiment without departing from the scope of the invention as set-forth in the appended Claims.

What is claimed is:

1. A powder spreadability inspection tool for evaluating a spreadability of an additive manufacturing (AM) powder, the powder spreadability inspection tool comprising:
    a powder support surface having a visual inspection area;
    a spreader system including a spreader implement movable relative to the powder support surface along a path passing over the visual inspection area; and
    a powder dispenser configured to dispense a metered volume of an AM powder sample onto the powder support surface in the path of the spreader implement, which spreads the AM powder sample across the visual inspection area to enable a visual evaluation of powder spreadability,
    wherein the powder spreadability inspection tool excludes any energy source capable of directing an energy beam at the powder support surface for fusing or sintering the AM powder sample, and wherein the powder spreadability inspection tool further comprises visual indicia of powder spreadability quality appearing on or adjacent the visual inspection area, the visual indicia of powder spreadability quality comprising color-coded regions of the visual inspection area.

2. The powder spreadability inspection tool of claim 1 wherein the spreader implement comprises a lower edge spaced from the powder support surface by a vertical gap, as taken along a first axis orthogonal to the powder support surface; and
    wherein the vertical gap has a substantially constant height, as taken along a second axis perpendicular to the first axis and parallel to the powder support surface.

3. The powder spreadability inspection tool of claim 1 wherein the spreader implement comprises a lower edge spaced from the powder support surface by a vertical gap having a height, as taken along a first axis orthogonal to the powder support surface; and
    wherein the spreader implement further comprises a gap adjustment mechanism enabling the height of the vertical gap to be adjusted.

4. The powder spreadability inspection tool of claim 1 wherein the spreader system further comprises a spreader actuator configured to move the spreader system along a translational axis substantially parallel to the powder support surface.

5. The powder spreadability inspection tool of claim 1 wherein the spreader implement progresses from a start position to an end position when traveling along the path, and wherein the visual indicia of powder spreadability quality comprise:
    a visual indicator of a poor powder spreadability adjacent the start position; and
    a visual indicator of good powder spreadability adjacent the end position.

6. The powder spreadability inspection tool of claim 1 wherein the spreader system further comprises a linear guide system, which confines the spreader implement to linear motion as the spreader implement moves relative to the powder support surface.

7. The powder spreadability inspection tool of claim 1 further comprising:
    a camera having a field of view encompassing the visual inspection area;
    a display device; and
    a processor coupled to the camera and configured to:
        analyze image data received from the camera of the AM powder sample, when spread across the visual inspection areas;
        assess the spreadability of the AM powder sample based upon the analysis of the image data; and
        indicate results of the assessment on the display device.

8. The powder spreadability inspection tool of claim 1 further comprising an electrically-grounded plate defining the powder support surface.

9. A powder spreadability inspection tool for evaluating a spreadability of an additive manufacturing (AM) powder, the powder spreadability inspection tool comprising:
- a powder support surface having a visual inspection area;
- a spreader system configured to spread the AM powder over the visual inspection area as a powder layer having a substantially uniform thickness; and
- visual indicia on the powder support surface correlating coverage of the visual inspection area of the powder layer with a spreadability quality of the AM powder,
- wherein the powder spreadability inspection tool excludes any energy source capable of directing an energy beam at the powder support surface for fusing or sintering the powder layer.

10. The powder spreadability inspection tool of claim 9 wherein the visual indicia comprise color-coded regions of the visual inspection area.

11. The powder spreadability inspection tool of claim 9 wherein the spreader system comprises:
- a wiper blade spaced from the powder support surface by a vertical gap, as taken along an axis orthogonal to the powder support surface; and
- a spreader actuator configured to move the wiper blade from a start position to an end position to spread the powder layer over the visual inspection area.

12. The powder spreadability inspection tool of claim 11 wherein the visual indicia comprise:
- a visual indicator of a poor powder spreadability adjacent the start position; and
- a visual indicator of good powder spreadability adjacent the end position.

13. The powder spreadability inspection tool of claim 11 wherein the spreader system further comprises a gap adjustment mechanism enabling a height of the vertical gap to be adjusted.

14. The powder spreadability inspection tool of claim 11 further comprising a powder dispenser configured to selectively dispense the AM powder in a predetermined amount ahead of the wiper blade.

15. The powder spreadability inspection tool of claim 11 wherein the wiper blade travels along a substantially linear path, which is parallel to the powder support surface, when moving from the start position to the end position.

16. A method for evaluating a spreadability of an additive manufacturing (AM) powder, the method carried-out utilizing a powder spreadability inspection tool including a spreader implement and a powder support surface having a visual inspection area, the method comprising:
- dispensing a predetermined amount of an AM powder sample onto the powder support surface;
- utilizing the spreader implement to spread the AM powder sample across the visual inspection area, the AM powder sample spread in a powder layer having a substantially uniform thickness; and
- visually assessing the spreadability of the AM powder sample based, at least in part, on coverage of the visual inspection area by the powder layer,
- wherein the powder spreadability inspection tool used for the steps of dispensing and spreading excludes any energy source capable of directing an energy beam at the powder support surface for fusing or sintering the powder layer, and wherein the method excludes any step of fusing or sintering the powder layer.

17. The method of claim 16 wherein the spreader implement comprises a lower edge spaced from the powder support surface by a vertical gap having a height, as taken along a first axis orthogonal to the powder support surface; and
- wherein dispensing comprises dispensing the AM powder sample in a predetermined amount sufficient to cover at least a majority of the visual inspection area, given the height of the vertical gap, when the AM powder sample possesses an optimal spreadability.

18. The method of claim 16 wherein visually assessing comprises:
- capturing image data of the powder layer utilizing a camera having a field-of-view encompassing the visual inspection area;
- utilizing a processor, which is coupled to the camera, to assess the spreadability of the AM powder sample based upon the analysis of the image data; and
- displaying results of the assessment on a display device coupled to the processor.

* * * * *